(12) United States Patent
Dhawan et al.

(10) Patent No.: US 12,241,011 B2
(45) Date of Patent: Mar. 4, 2025

(54) POLYAMINE-POLYESTERS AS CORROSION INHIBITION

(71) Applicant: Ecolab USA Inc., St. Paul, MN (US)

(72) Inventors: Ashish Dhawan, Aurora, IL (US); Jeremy Moloney, Katy, TX (US); Carter Martin Silvernail, Lakeville, MN (US)

(73) Assignee: Ecolab USA Inc., St. Paul, MN (US)

( * ) Notice: Subject to any disclaimer, the term of this patent is extended or adjusted under 35 U.S.C. 154(b) by 277 days.

(21) Appl. No.: 17/817,795

(22) Filed: Aug. 5, 2022

(65) Prior Publication Data

US 2023/0076540 A1 Mar. 9, 2023

Related U.S. Application Data

(60) Provisional application No. 63/203,957, filed on Aug. 5, 2021.

(51) Int. Cl.
 *C11D 11/00* (2006.01)
 *C07C 219/08* (2006.01)
 (Continued)

(52) U.S. Cl.
 CPC ............ *C09K 15/20* (2013.01); *C07C 219/08* (2013.01); *C11D 3/0015* (2013.01); *C11D 3/30* (2013.01);
 (Continued)

(58) Field of Classification Search
 CPC ..... C11D 11/0017; C11D 3/0015; C11D 3/30; C07C 219/08; C09K 15/20
 See application file for complete search history.

(56) References Cited

U.S. PATENT DOCUMENTS

| | | |
|---|---|---|
| 1,901,565 A | 3/1933 | Pasternack et al. |
| 2,662,073 A | 12/1953 | Mehltretter et al. |
| (Continued) | | |

FOREIGN PATENT DOCUMENTS

| | | |
|---|---|---|
| CN | 111574711 A | 8/2020 |
| DE | 2522219 B1 | 11/1976 |
| (Continued) | | |

OTHER PUBLICATIONS

International Search Report and Written Opinion dated Oct. 27, 2022 relating to PCT/US2022/039526, 12 pages.

*Primary Examiner* — Liam J Heincer
*Assistant Examiner* — M. Reza Asdjodi
(74) *Attorney, Agent, or Firm* — Stinson LLP

(57) ABSTRACT

Compounds, compositions and methods are provided for reducing, inhibiting, or preventing corrosion of a surface, using a polyester polyamine compound. The polyester polyamine compound having a structure corresponding to Formula 1 or 2, or a salt thereof:

(1)

(Continued)

-continued

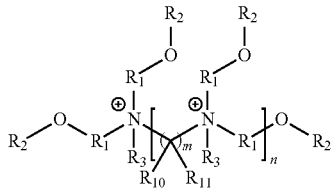
(2)

wherein $R_1$ is independently alkylene; $R_2$ is independently hydrogen or $-COR_4$; $R_3$ is independently alkyl, alkenyl, aryl, or alkaryl; $R_4$ is independently alkyl or alkenyl; $R_{10}$ and $R_{11}$ are each independently hydrogen, alkyl, or alkaryl; m is an integer from 1 to 10; n is an integer from 3 to 10; and wherein at least one $R_2$ is $-COR_4$.

20 Claims, 3 Drawing Sheets

(51) Int. Cl.
 *C09K 15/20* (2006.01)
 *C11D 3/00* (2006.01)
 *C11D 3/30* (2006.01)
 *C23F 11/14* (2006.01)
(52) U.S. Cl.
 CPC ......... *C23F 11/141* (2013.01); *C11D 2111/12* (2024.01)

(56) References Cited

U.S. PATENT DOCUMENTS

| | | | |
|---|---|---|---|
| 2,752,334 A | 6/1956 | Walton | |
| 4,092,253 A | 5/1978 | Cuntze et al. | |
| 4,386,000 A | 5/1983 | Turner et al. | |
| 4,891,160 A | 1/1990 | Vander Meer | |
| 5,521,293 A | 5/1996 | Vermeer et al. | |
| 5,750,733 A | 5/1998 | Vermeer et al. | |
| 6,200,938 B1 | 3/2001 | Perella et al. | |
| 6,211,139 B1 | 4/2001 | Keys et al. | |
| 6,235,914 B1 | 5/2001 | Steiger et al. | |
| 6,376,455 B1 | 4/2002 | Friedli et al. | |
| 6,562,780 B2 | 5/2003 | Bermejo et al. | |
| 6,979,440 B2 | 12/2005 | Shefer et al. | |
| 6,995,131 B1 | 2/2006 | Frankenbach et al. | |
| 7,431,845 B2 | 10/2008 | Manek et al. | |
| 7,786,179 B2 | 8/2010 | Talingting-Pabalan et al. | |
| 8,268,957 B2 | 9/2012 | Liu et al. | |
| 8,540,885 B2 | 9/2013 | Ebert et al. | |
| 8,714,249 B1 | 5/2014 | Tang | |
| 9,034,813 B2 | 5/2015 | Man et al. | |
| 9,103,039 B2 | 8/2015 | Jenkins et al. | |
| 9,410,076 B2 | 8/2016 | Reddy et al. | |
| 9,944,878 B2 | 4/2018 | Butke et al. | |
| 10,005,951 B2 | 6/2018 | Vo et al. | |
| 10,538,719 B2 | 1/2020 | Sivik et al. | |
| 2005/0014672 A1 | 1/2005 | Arif | |
| 2009/0105109 A1 | 4/2009 | Lant et al. | |
| 2015/0307788 A1 | 10/2015 | McDaniel et al. | |
| 2016/0158121 A1 * | 6/2016 | Lei | C11D 17/0039 424/70.17 |
| 2016/0166480 A1 * | 6/2016 | Lei | A61K 8/731 510/159 |
| 2016/0177162 A1 | 6/2016 | Nguyen et al. | |
| 2017/0247798 A1 * | 8/2017 | Moloney | C23F 11/145 |
| 2018/0148632 A1 | 5/2018 | Bennett et al. | |
| 2019/0223434 A1 | 7/2019 | Balasubramanian et al. | |
| 2019/0390141 A1 | 12/2019 | Li et al. | |
| 2020/0071265 A1 | 3/2020 | Dhawan et al. | |
| 2020/0199485 A1 | 6/2020 | Baum | |
| 2023/0076540 A1 * | 3/2023 | Dhawan | C23F 11/141 |
| 2023/0096673 A1 * | 3/2023 | Dhawan | C23F 11/173 422/9 |

FOREIGN PATENT DOCUMENTS

| | | | | |
|---|---|---|---|---|
| EP | 0131865 B1 | 9/1988 | | |
| EP | 0 550 281 A2 | 7/1993 | | |
| GB | 866408 | 4/1961 | | |
| GB | 866408 A * | 4/1961 | | |
| WO | 96/29977 | 10/1996 | | |
| WO | 97/42281 | 11/1997 | | |
| WO | 00/58427 | 10/2000 | | |
| WO | 2009/043708 A1 | 4/2009 | | |
| WO | 2009/094221 A1 | 7/2009 | | |
| WO | WO-2012028542 A1 * | 3/2012 | ........... C08G 63/668 | |
| WO | WO-2012089649 A1 * | 7/2012 | ........... C09D 5/086 | |
| WO | 2013/092440 | 6/2013 | | |
| WO | WO-2013092440 A1 * | 6/2013 | ............... C09K 8/52 | |
| WO | 2017/147487 A1 | 8/2017 | | |
| WO | 2020/204689 A1 | 10/2020 | | |

* cited by examiner

POLYAMINE-POLYESTERS AS CORROSION INHIBITION

CROSS REFERENCE TO RELATED APPLICATIONS

This application claims priority to U.S. Provisional Patent Application Ser. No. 63/203,957 filed on Aug. 5, 2021, the disclosure of which is incorporated herein by reference in its entirety.

FIELD OF THE INVENTION

Compounds, compositions and methods are provided for reducing, inhibiting, or preventing corrosion of a surface, using a polyester polyamine compound. The polyester polyamine compound having a structure corresponding to Formula 1 or 2, or a salt thereof.

BACKGROUND OF THE INVENTION

Corrosion of metal surfaces in aqueous media has long been a problem for industries such as the oil and gas industry, food/beverage industry, wash/sanitizing industry, pulp and paper, power generation, manufacturing, and utilities. For example, it is well known that during the production of oil and gas several other corrosive components are present such as brines, organic acids, carbon dioxide, hydrogen sulfide, and microorganisms. These aggressive constituents can cause severe corrosion as evidenced by surface pitting, embrittlement, and general loss of metal. The metallic surfaces can be composed of high alloy steels including chrome steels, ferritic alloy steels, austenitic stainless steels, precipitation-hardened stainless steels, and high nickel content steels, copper, and carbon steels.

In the food/beverage and wash/sanitizing industry, solutions such as sodium hypochlorite solutions are commonly used and are highly effective as bleaches and sanitizers for cleaning a variety of surfaces. However, sodium hypochlorite solutions are corrosive to many treated surfaces, in particular, metal surfaces become highly corroded.

There are several mechanisms responsible for corrosion of metals. In corrosive water systems, the overall corrosion rate is controlled by the reduction of oxygen inhibiting the cathodic reaction. However, the most robust and cost effective water treatment programs include both anodic and cathodic inhibitors to block reactions at both the anode and the cathode.

Corrosion inhibitors are usually surface-active compounds that form protective coatings on the surface of metals and suppress corrosion by preventing or reducing contact of the corrosive species to the pipeline surface. Common corrosion inhibitors are composed of amines, condensation products of fatty acids with polyamines, imidazolines, and/or quaternary ammonium compounds. Among the most frequently used corrosion inhibitors in crude oil and natural gas extraction are imidazoline derivatives and benzyldimethylalkylammonium chlorides.

Many regions around the world are extremely conscious about the potential harmful effects of chemical use in environmentally sensitive areas. Components in such products are often evaluated for their potential to bioaccumulate in organisms, their ability to biodegrade, and their toxicity in select aquatic species. The combination of these tests allows the regional authorities to assess the potential danger to the area of interest and permit or deny the use of the chemical.

Many corrosion inhibitor formulations have components that are toxic, bioaccumulate, or have biodegradation profiles that are not advantageous for the environment. As such, the development of new, high-performance actives that meet the stringent environmental regulations of these regions is needed.

BRIEF SUMMARY OF THE INVENTION

Disclosed herein are polyester polyamine compounds, the polyester polyamine compounds corresponding to the structure of Formula 1 or 2, or a salt thereof:

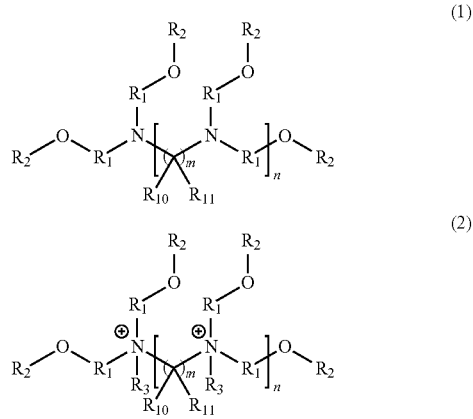

wherein $R_1$ is independently alkylene; $R_2$ is independently hydrogen or $-COR_4$; $R_3$ is independently alkyl, alkenyl, aryl, or alkaryl; $R_4$ is independently alkyl or alkenyl; $R_{10}$ and $R_{11}$ are each independently hydrogen, alkyl, or alkaryl; m is an integer from 1 to 10; n is an integer from 3 to 10; and wherein at least one $R_2$ is $-COR_4$.

For the compounds of Formula 1 and 2, $R_1$ is $C_1$ to $C_8$ alkylene; further, $R_1$ is $-CH_2CH_2-$ or $-CH_2CH(CH_3)-$.

For the compounds of Formula 1 and 2, from about 50% to about 100% of $R_2$ are $-COR_4$.

Additionally, the compounds of Formula 1 and 2 have $R_4$ of $C_{12}$ to $C_{22}$ alkyl.

The compounds of Formula 1 and 2 also have $COR_4$ being derived from a fatty acid. The fatty acid can be stearic acid, palmitic acid, oleic acid, behenic acid, myristic acid, or a combination thereof.

Also, the polyester polyamine compound of Formula 1 and 2 has $R_3$ of $C_1$ to $C_4$ alkyl or alkaryl; preferably, $R_3$ is methyl, ethyl, or benzyl.

The polyester polyamine compounds of Formula 1 and 2 have m of an integer from 2 to 6.

Further, the polyester polyamine compounds of Formula 1 and 2 have $R_{10}$ of hydrogen and $R_{11}$ of hydrogen or methyl.

Yet further, the polyester polyamine compounds of Formula 1 and 2 have n of an integer of 3, 4, or 5.

The polyester polyamine compounds of Formula 1 and 2 can be a halogen salt or an acetate salt; preferably, the polyester polyamine compound is a chloride salt.

Also disclosed herein are corrosion inhibitor compositions comprising the polyester polyamine compounds described herein.

The corrosion inhibitor composition comprises from about 0.1 to about 20 wt. % of the polyester polyamine compound based on the total weight of the composition.

The corrosion inhibitor composition further comprises one or more additional corrosion inhibitors, solvents, asphaltene inhibitors, paraffin inhibitors, scale inhibitors, emulsifiers, water clarifiers, dispersants, emulsion breakers, gas hydrate inhibitors, biocides, pH modifiers, or surfactants.

Also disclosed are methods for inhibiting corrosion of a surface, the method comprising adding a composition comprising the polyester polyamine compounds disclosed herein or the corrosion inhibitor compositions disclosed herein to a fluid which contacts the surface.

The polyester polyamine compound is present in the fluid in an amount from about 1 ppm to about 5000 ppm; preferably, from about 10 ppm to about 50 ppm.

The methods disclosed herein have the surface is part of equipment used in an industrial system.

The industrial system is a water recirculating system, a cooling water system, a boiler water system, a pulp slurry, a papermaking process, a ceramic slurry, a mixed solid/liquid system, or an oil-field system.

For the methods described herein, the surface is part of equipment used in the production, transportation, storage, and/or separation of crude oil or natural gas.

In the methods disclosed, the equipment comprises a pipeline, a storage vessel, a downhole injection tubing, a flow line, or an injection line.

For the methods described herein, the fluid is used in the operation of the industrial system.

In the methods, the fluid comprises seawater, produced water, fresh water, brackish water, drilling fluid, completion fluid, or a combination thereof.

Further disclosed is a fabric softener composition comprising the polyester polyamine compound of Formula 1 or 2 disclosed herein.

Also, the fabric softener composition comprises from about 0.1 to about 50 wt. % of the polyester polyamine compound based on the total weight of the composition.

The fabric softener compositions can further comprise one or more additional fabric softeners or cosofteners, silicones, solvents, emulsifiers, dispersants, emulsion breakers, biocides, pH modifiers, or surfactants.

Also disclosed are methods for treating fabric comprising the polyester polyamine compounds of Formula 1 or 2 or the fabric softener composition disclosed herein to a fluid which contacts the fabric.

In the methods described herein, the polyester polyamine compound is present in the fluid in an amount from about 1 ppm to about 5000 ppm; preferably, from about 20 ppm to about 200 ppm.

Additionally, the disclosure is directed to a fabric antistatic composition, a fabric conditioner composition, or a relaxant composition comprising the polyester polyamine compound of Formula 1 or 2.

The fabric antistatic, fabric conditioner, or relaxant compositions comprise from about 0.1 to about 50 wt. % of the polyester polyamine compound of Formula 1 or 2 based on the total weight of the composition.

Other objects and features will be in part apparent and in part pointed out hereinafter.

DETAILED DESCRIPTION OF THE INVENTION

Figure 1:
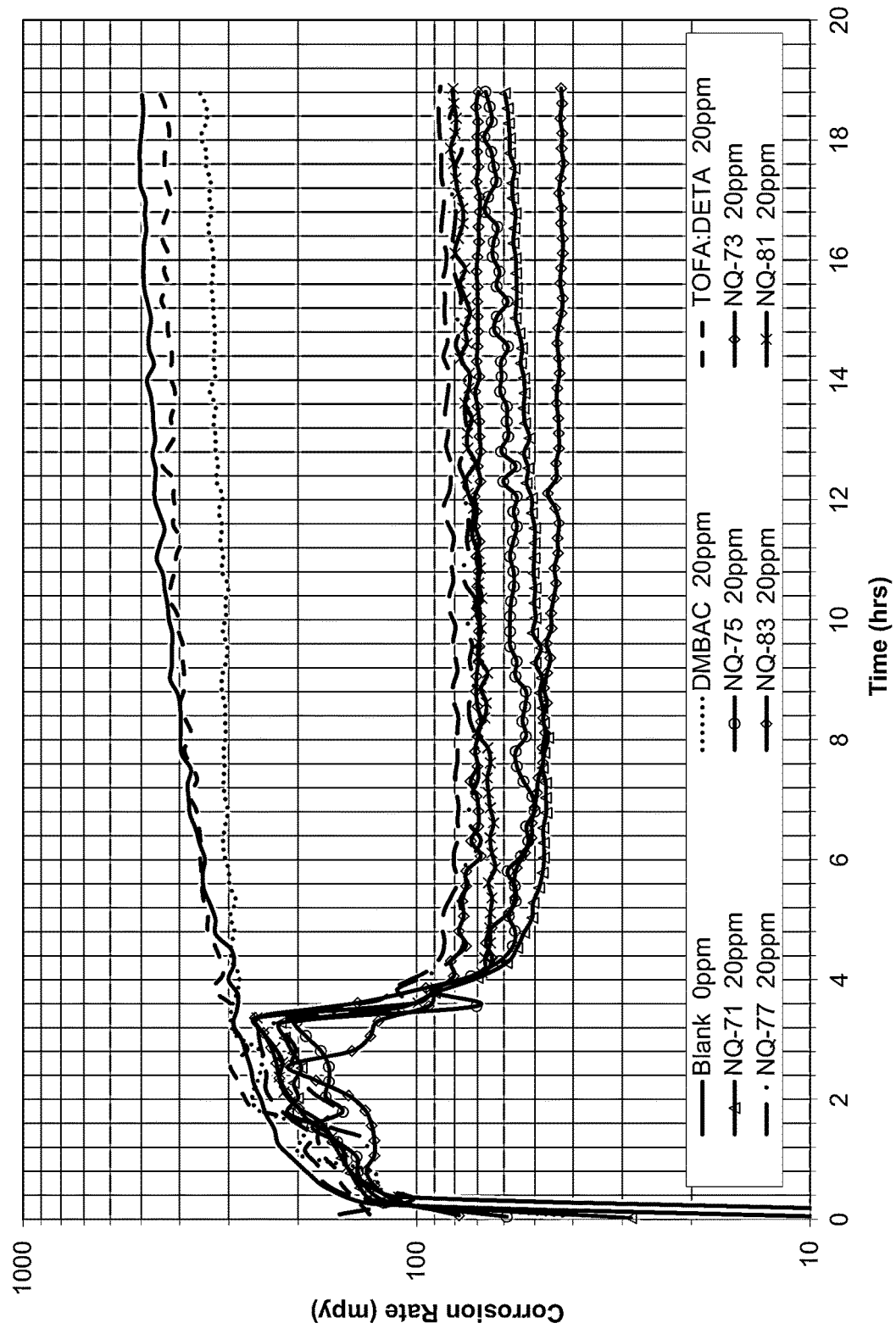
FIG. 1 is a graph of the corrosion rate (mpy) versus time (hours) for various corrosion inhibitor compositions.

Disclosed herein are compounds and compositions, methods of using the compounds and compositions for inhibiting corrosion, and processes for their preparation. The compounds and compositions are useful for inhibiting corrosion in industrial systems. The compositions and methods are particularly useful for inhibiting corrosion in equipment used in the production, transportation, storage, and separation of crude oil and natural gas. The compositions include a class of polyester polyamine corrosion inhibitors that are effective and environmentally friendly.

A corrosion inhibitor according to the present disclosure may comprise a hydrolysable functional group. Illustrative, non-limiting examples of hydrolysable functional groups are carboxylic esters and amides that can yield carboxylic acid products. Having the hydrolysable functionality incorporated into the molecular structure of the corrosion inhibitor composition allows cleavage and enhanced degradation under certain industrial conditions. The presently disclosed corrosion inhibitor compositions may also have an improved toxicological profile when compared to currently available quaternary ammonium chlorides, such as those used in the oil field industry.

Disclosed herein are polyester polyamine compounds, the polyester polyamine compounds corresponding to the structure of Formula 1 or 2, or a salt thereof:

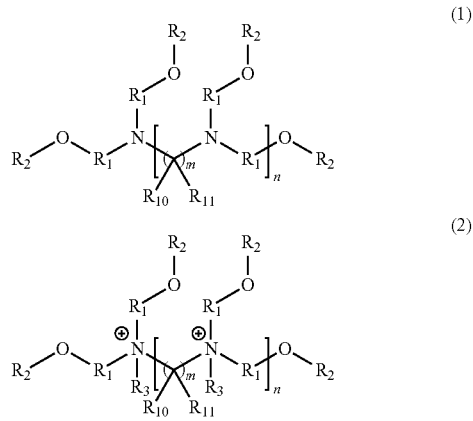

wherein $R_1$ is independently alkylene; $R_2$ is independently hydrogen or —$COR_4$; $R_3$ is independently alkyl, alkenyl, aryl, or alkaryl; $R_4$ is independently alkyl or alkenyl; $R_{10}$ and $R_{11}$ are each independently hydrogen, alkyl, or alkaryl; m is an integer from 1 to 10; n is an integer from 3 to 10; and wherein at least one $R_2$ is —$COR_4$.

For the compounds of Formula 1 and 2, $R_1$ is $C_1$ to $C_8$ alkylene; further, $R_1$ is —$CH_2CH_2$— or —$CH_2CH(CH_3)$—.

For the compounds of Formula 1 and 2, from about 50% to about 100% of $R_2$ are —$COR_4$.

Additionally, the compounds of Formula 1 and 2 have $R_4$ of $C_{12}$ to $C_{22}$ alkyl.

The compounds of Formula 1 and 2 also have $COR_4$ being derived from a fatty acid. The fatty acid can be stearic acid, palmitic acid, oleic acid, behenic acid, myristic acid, or a combination thereof.

Also, the polyester polyamine compound of Formula 1 and 2 has $R_3$ of $C_1$ to $C_4$ alkyl or alkaryl; preferably, $R_3$ is methyl, ethyl, or benzyl.

The polyester polyamine compounds of Formula 1 and 2 have m of an integer from 2 to 6.

Further, the polyester polyamine compounds of Formula 1 and 2 have $R_{10}$ of hydrogen and $R_{11}$ of hydrogen or methyl.

Yet further, the polyester polyamine compounds of Formula 1 and 2 have n of an integer of 3, 4, or 5.

The polyester polyamine compounds of Formula 1 and 2 can be a halogen salt or an acetate salt; preferably, the polyester polyamine compound is a chloride salt.

Also disclosed herein are corrosion inhibitor compositions comprising the polyester polyamine compounds described herein.

The corrosion inhibitor composition comprises from about 0.1 to about 20 wt. % of the polyester polyamine compound based on the total weight of the composition.

The corrosion inhibitor composition further comprises one or more additional corrosion inhibitors, solvents, asphaltene inhibitors, paraffin inhibitors, scale inhibitors, emulsifiers, water clarifiers, dispersants, emulsion breakers, gas hydrate inhibitors, biocides, pH modifiers, or surfactants.

Also disclosed are methods for inhibiting corrosion of a surface, the method comprising adding a composition comprising the polyester polyamine compounds disclosed herein or the corrosion inhibitor compositions disclosed herein to a fluid which contacts the surface.

The polyester polyamine compound is present in the fluid in an amount from about 1 ppm to about 5000 ppm; preferably, from about 10 ppm to about 50 ppm.

The methods disclosed herein have the surface is part of equipment used in an industrial system.

The industrial system is a water recirculating system, a cooling water system, a boiler water system, a pulp slurry, a papermaking process, a ceramic slurry, a mixed solid/liquid system, or an oil-field system.

For the methods described herein, the surface is part of equipment used in the production, transportation, storage, and/or separation of crude oil or natural gas.

In the methods disclosed, the equipment comprises a pipeline, a storage vessel, a downhole injection tubing, a flow line, or an injection line.

For the methods described herein, the fluid is used in the operation of the industrial system.

In the methods, the fluid comprises seawater, produced water, fresh water, brackish water, drilling fluid, completion fluid, or a combination thereof.

Further disclosed is a fabric softener composition comprising the polyester polyamine compound of Formula 1 or 2 disclosed herein.

Also, the fabric softener composition comprises from about 0.1 to about 50 wt. % of the polyester polyamine compound based on the total weight of the composition.

The fabric softener compositions can further comprise one or more additional fabric softeners or cosofteners, silicones, solvents, emulsifiers, dispersants, emulsion breakers, biocides, pH modifiers, or surfactants.

Also disclosed are methods for treating fabric comprising the polyester polyamine compounds of Formula 1 or 2 or the fabric softener composition disclosed herein to a fluid which contacts the fabric.

In the methods described herein, the polyester polyamine compound is present in the fluid in an amount from about 1 ppm to about 5000 ppm; preferably, from about 20 ppm to about 200 ppm.

Additionally, the disclosure is directed to a fabric antistatic composition, a fabric conditioner composition, or a relaxant composition comprising the polyester polyamine compound of Formula 1 or 2.

The fabric antistatic, fabric conditioner, or relaxant compositions comprise from about 0.1 to about 50 wt. % of the polyester polyamine compound of Formula 1 or 2 based on the total weight of the composition.

The anticorrosion compounds of Formula 1 or 2 can be prepared using the following reaction scheme.

For the methods described herein, the anticorrosion compound of Formula 1 or 2 can be present in an amount from about 0.1 ppm to about 10000 ppm, from about 0.1 ppm to about 5000 ppm, from about 0.1 ppm to about 3000 ppm, from about 0.1 ppm to about 2000 ppm, from about 0.1 ppm to about 1500 ppm, from about 0.1 ppm to about 1000 ppm, from about 0.1 ppm to about 500 ppm, from about 0.5 ppm to about 5000 ppm, from about 0.5 ppm to about 4000 ppm, from about 0.5 ppm to about 3000 ppm, from about 0.5 ppm to about 2500 ppm, from about 0.5 ppm to about 2000 ppm, from about 0.5 ppm to about 1500 ppm, from about 0.5 ppm to about 1000 ppm, from about 0.5 ppm to about 500 ppm, from about 1 ppm to about 5000 ppm, from about 1 ppm to about 4000 ppm, from about 1 ppm to about 3000 ppm, from about 1 ppm to about 2500 ppm, from about 1 ppm to about 2000 ppm, from about 1 ppm to about 1500 ppm, from about 1 ppm to about 1000 ppm, from about 1 ppm to about 500 ppm, from about 1 ppm to about 100 ppm, or from about 1 ppm to about 10 ppm, based on the total weight of the fluid in contact with the surface.

The compounds of Formula 1 and 2 were prepared by reacting an alkoxylated polyamine with specified amounts of carboxylic acid compounds, particularly fatty acids. As shown in the following scheme, the alkoxylated polyamine is reacted with a carboxylic acid to form an alkoxylated and esterified polyamine depending on the relative amounts of the alkoxylated polyamine and carboxylic acid used in the reaction. After the esterification reaction, the esterified polyamine could be quaternized with an alkyl group by reaction with an alkyl halide or other nucleophilic alkyl group.

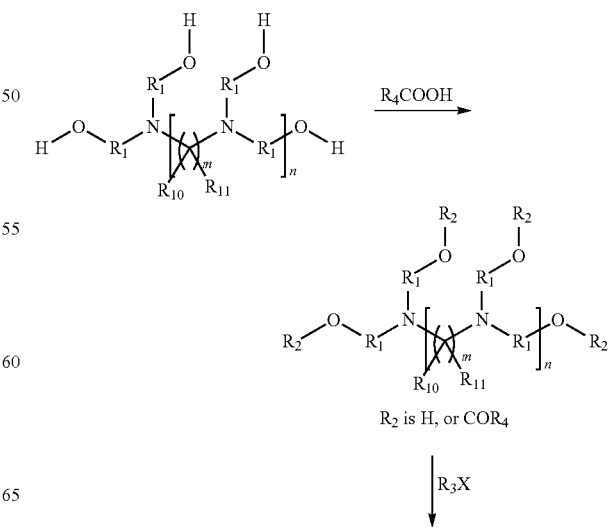

-continued

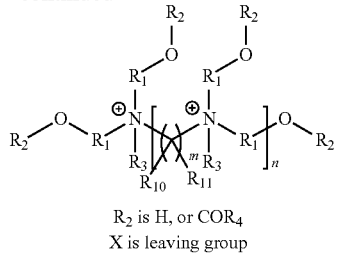

R₂ is H, or COR₄
X is leaving group

For example, an polyhydroxyl polyamine (e.g., ethoxylated tetraethylenetriamine) is added to a three-necked round bottom flask equipped with a Dean Stark apparatus, nitrogen inlet, magnetic stir bar, and a condenser. The flask is heated to a temperature of from about 100 to 140° C. and water present in the starting material is removed using the Dean Stark apparatus. A fatty acid is then introduced into the flask. The reaction mixture is heated for at least 6 hours at about 150 to 200° C. to remove water of reaction using the Dean Stark apparatus. The product obtained from this step is a mixture of mono-, di-, tri-, tetra-, penta-, and hexa-esterified products. The average molar ratio of polyamine to fatty acid was from about 1 to about 4.

Different compounds were created by varying amounts of the fatty acid with respect to the polyhydroxy polyamine compound.

The esterified polyamines are then quaternized by charging the esterified polyamine and a solvent (e.g., isopropanol (IPA)) into a Parr reactor and agitating the mixture. A vacuum of 28 inches of mercury is applied for 5 minutes and the reactor is heated to about 50 to 70° C. When the temperature reaches 65° C., an alkyl halide (e.g., methyl chloride ($CH_3Cl$)) is charged to 10 psig. The temperature is increased to 80° C. and the alkyl halide pressure is maintained at less than 40 psig. When the alkyl halide addition is complete, the temperature is maintained at about 90 to 95° C. for an hour. The total amine value (TAV) and acid value (AV) of the reaction mixture is checked (<2%). A strong base (e.g., sodium hydroxide (NaOH, 50% aqueous)) is added to adjust the acid value (to <2%) or extra alkyl halide is charged to adjust the TAV (to <2%), and the reaction mixture is reacted at about 90° C. for an additional hour. On completion, the reaction mixture is cooled to 50° C. and the pH is adjusted to 5.5-8.5 with 50% strong base solution. The reaction mixture is mixed well and a slight vacuum (about 12 inches of mercury) is applied to the reaction mixture for 5 minutes. The non-volatile residue (NVR, Mettler method) measurement is adjusted to 50% with solvent.

The anti-corrosion compound of Formula 1 or 2 can be contained in an anti-corrosion composition that further comprises one or more additional corrosion inhibitors, an organic solvent, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

The anti-corrosion composition described herein comprises from about 0.1 to about 20 wt. % of one or more compounds of formula 1 or 2 in a solvent system.

The organic solvent can comprise an alcohol, a hydrocarbon, a ketone, an ether, an alkylene glycol, a glycol ether, an amide, a nitrile, a sulfoxide, an ester, or any combination thereof, and the composition optionally comprises water.

Preferably, the organic solvent comprises methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

A compound used to enhance the corrosion performance of the composition can also be included in the anticorrosion composition. For example, thioglycolic acid, 3,3'-dithiopropioinic acid, thiosulfate, thiourea, 2-mercaptoethanol, L-cysteine, tert-butyl mercaptan, or a combination thereof can be included in the anticorrosion composition.

The methods described herein can have the surface be part of equipment used in an industrial system. Preferably, the industrial system is a water recirculating system, a cooling water system, a boiler water system, a pulp slurry, a papermaking process, a ceramic slurry, a mixed solid/liquid system, or an oil-field system.

The methods can have the surface be part of equipment used in the production, transportation, storage, and/or separation of crude oil or natural gas. Preferably, the equipment comprises a pipeline, a storage vessel, downhole injection tubing, a flow line, or an injection line.

The methods described herein can have the fluid be used in the operation of the industrial system.

The fluid can comprise seawater, produced water, fresh water, brackish water, drilling fluid, completion fluid, or a combination thereof.

Another aspect of the invention is a composition for inhibiting corrosion at a surface. The composition comprises an effective amount of the compound of formula 1 or 2 and a component comprising an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof.

The composition can comprise, for example, from about 0.1 to about 20 wt. % of one or more compounds of formula 1 or 2 and from about 80 to about 99.9 wt. % of the component; from about 0.1 to about 20 wt. % of one or more compounds of formula 1 or 2, from about 1 to about 60 wt. % of the component and from about 20 to about 98.9 wt. % water; from about 10 to about 20 wt. % of one or more compounds of formula 1 or 2, from about 30 to about 40 wt. % of the component and from about 40 to about 60 wt. % water; or from about 15 to about 20 wt. % of one or more compounds of formula 1 or 2, from about 1 to about 10 wt. % of the component and from about 70 to about 84 wt. % water.

The component of the composition can comprise an organic solvent. The composition can comprise from about 1 to 80 wt. %, from about 5 to 50 wt. %, or from about 10 to 35 wt. % of the one or more organic solvents, based on total weight of the composition. The organic solvent can comprise an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

In addition to the component, the composition can comprise water.

The component of the composition can comprise a corrosion inhibitor in addition to the one or more compounds of formula 1 or 2. The composition can comprise from about 0.1 to 20 wt. %, 0.1 to 10 wt. %, or 0.1 to 5 wt. % of the one or more additional corrosion inhibitors, based on total weight of the composition. A composition of the invention can comprise from 0 to 10 percent by weight of the one or more additional corrosion inhibitors, based on total weight of the composition. The composition can comprise 1.0 wt. %, 1.5 wt. %, 2.0 wt. %, 2.5 wt. %, 3.0 wt. %, 3.5 wt. %, 4.0 wt. %, 4.5 wt. %, 5.0 wt. %, 5.5 wt. %, 6.0 wt. %, 6.5 wt. %, 7.0 wt. %, 7.5 wt. %, 8.0 wt. %, 8.5 wt. %, 9.0 wt. %, 9.5 wt. %, 10.0 wt. %, 10.5 wt. %, 11.0 wt. %, 11.5 wt. %, 12.0 wt. %, 12.5 wt. %, 13.0 wt. %, 13.5 wt. %, 14.0 wt. %, 14.5 wt. %, or 15.0 wt. % by weight of the one or more additional corrosion inhibitors, based on total weight of the composition. Each system can have its own requirements, and the weight percent of one or more additional corrosion inhibitors in the composition can vary with the system in which it is used.

The one or more additional corrosion inhibitors can comprise an imidazoline compound, a quaternary ammonium compound, a pyridinium compound, or a combination thereof.

The one or more additional corrosion inhibitor component can comprise an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (I) or an imidazoline derivative. Representative imidazoline derivatives include an imidazolinium compound of Formula (II) or a bis-quaternized compound of Formula (III).

The one or more additional corrosion inhibitor component can include an imidazoline of Formula (I):

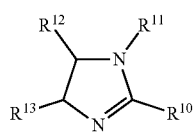

wherein $R^{10}$ is a $C_1$-$C_{20}$ alkyl or a $C_1$-$C_{20}$ alkoxyalkyl group; $R^{11}$ is hydrogen, $C_1$-$C_6$ alkyl, $C_1$-$C_6$ hydroxyalkyl, or $C_1$-$C_6$ arylalkyl; and $R^{12}$ and $R^{13}$ are independently hydrogen or a $C_1$-$C_6$ alkyl group. Preferably, the imidazoline includes an $R^{10}$ which is the alkyl mixture typical in tall oil fatty acid (TOFA), and $R^{11}$, $R^{12}$ and $R^{13}$ are each hydrogen.

The one or more additional corrosion inhibitor component can include an imidazolinium compound of Formula (II):

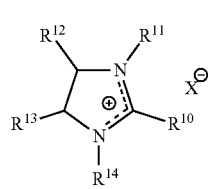

wherein $R^{10}$ is a $C_1$-$C_{20}$ alkyl or a $C_1$-$C_{20}$ alkoxyalkyl group; $R^{11}$ and $R^{14}$ are independently hydrogen, $C_1$-$C_6$ alkyl, $C_1$-$C_6$ hydroxyalkyl, or $C_1$-$C_6$ arylalkyl; $R^{12}$ and $R^{13}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The one or more additional corrosion inhibitors can comprise a bis-quaternized compound having the formula (III):

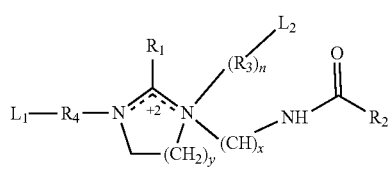

wherein:
$R_1$ and $R_2$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof;

$R_3$ and $R_4$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof;

$L_1$ and $L_2$ are each independently absent, H, —COOH, —SO$_3$H, —PO$_3$H$_2$, —COOR$_5$, —CONH$_2$, —CONHR$_5$, or —CON(R$_5$)$_2$;

$R_5$ is each independently a branched or unbranched alkyl, aryl, alkylaryl, alkylheteroaryl, cycloalkyl, or heteroaryl group having from 1 to about 10 carbon atoms;

n is 0 or 1, and when n is 0, $L_2$ is absent or H;

x is from 1 to about 10; and y is from 1 to about 5. Preferably, $R_1$ and $R_2$ are each independently $C_6$-$C_{22}$ alkyl, $C_8$-$C_{20}$ alkyl, $C_{12}$-$C_{18}$ alkyl, $C_{16}$-$C_{18}$ alkyl, or a combination thereof; $R_3$ and $R_4$ are $C_1$-$C_{10}$ alkylene, $C_2$-$C_8$ alkylene, $C_2$-$C_6$ alkylene, or $C_2$-$C_3$ alkylene; n is 0 or 1; x is 2; y is 1; $R_3$ and $R_4$ are —C$_2$H$_2$—; $L_1$ is —COOH, —SO$_3$H, or —PO$_3$H$_2$; and $L_2$ is absent, H, —COOH, —SO$_3$H, or —PO$_3$H$_2$. For example, $R_1$ and $R_2$ can be derived from a mixture of tall oil fatty acids and are predominantly a mixture of $C_{17}H_{33}$ and $C_{17}H_{31}$ or can be $C_{16}$-$C_{18}$ alkyl; $R_3$ and $R_4$ can be $C_2$-$C_3$ alkylene such as —C$_2$H$_2$—; n is 1 and $L_2$ is —COOH or n is 0 and $L_2$ is absent or H; x is 2; y is 1; $R_3$ and $R_4$ are —C$_2$H$_2$—; and $L_1$ is —COOH.

It should be appreciated that the number of carbon atoms specified for each group of formula (III) refers to the main chain of carbon atoms and does not include carbon atoms that may be contributed by substituents.

The one or more additional corrosion inhibitors can comprise a bis-quaternized imidazoline compound having the formula (III) wherein $R_1$ and $R_2$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R_4$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is —COOH, —$SO_3H$, or —$PO_3H_2$; and $L_2$ is absent or H. Preferably, a bis-quaternized compound has the formula (III) wherein $R_1$ and $R_2$ are each independently $C_{16}$-$C_{18}$ alkyl; $R_4$ is —$C_2H_2$—; x is 2; y is 1; n is 0; $L_1$ is —COOH, —$SO_3H$, or —$PO_3H_2$ and $L_2$ is absent or H.

The one or more additional corrosion inhibitors can be a quaternary ammonium compound of Formula (IV):

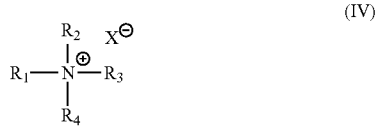

(IV)

wherein $R_1$, $R_2$, and $R_3$ are independently $C_1$ to $C_{20}$ alkyl, $R_4$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms, and X is Cl, Br or I. For the quaternary salts, $R^{5a}$, $R^{6a}$, $R^{7a}$, and $R^{8a}$ can each be independently alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula $[N^+R^{5a}R^{6a}R^{7a}R^{8a}][X^-]$ wherein $R^{5a}$, $R^{6a}$, $R^{7a}$, and $R^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The one or more additional corrosion inhibitor component can comprise a pyridinium salt such as those represented by Formula (V):

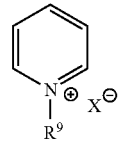

(V)

wherein $R^9$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The one or more additional corrosion inhibitor components can include additional corrosion inhibitors such as phosphate esters, monomeric or oligomeric fatty acids, or alkoxylated amines.

The one or more additional corrosion inhibitor component can comprise a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a more broad distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The one or more additional corrosion inhibitor component can include a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The one or more additional corrosion inhibitor component can comprise an alkoxylated amine. The alkoxylated amine can be an ethoxylated alkyl amine. The alkoxylated amine can be ethoxylated tallow amine.

The component of the composition can comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. The organic sulfur compound can constitute 0.5 to 15 wt. % of the composition, based on total weight of the composition, preferably about 1 to about 10 wt. % and more preferably about 1 to about 5 wt. %. The organic sulfur compound can constitute 1, 2, 3, 4, 5, 6, 7, 8, 9, 10, 11, 12, 13, 14 or 15 wt. % of the composition.

The composition can be substantially free of or free of any organic sulfur compound. A composition is substantially free of any organic sulfur compound if it contains an amount of organic sulfur compound less than 0.50 wt. % preferably less than 0.10 wt. %, and more preferably less than 0.01 wt. %.

The component of the composition can further include a demulsifier. Preferably, the demulsifier comprises an oxyalkylate polymer, such as a polyalkylene glycol. The demulsifier can constitute from about 0.1 to 10 wt. %, from about 0.5 to 5 wt. %, or from about 0.5 to 4 wt. % of the composition, based on total weight of the composition. The demulsifier can constitute 0.5, 1, 1.5, 2, 2.5, 3, 3.5, 4, 4.5 or 5 wt. % of the composition.

The component of the composition can include an asphaltene inhibitor. The composition can comprise from about 0.1 to 10 wt. %, from about 0.1 to 5 wt. %, or from about 0.5 to 4 wt. % of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The component of the composition can include a paraffin inhibitor. The composition can comprise from about 0.1 to 10 wt. %, from about 0.1 to 5 wt. %, or from about 0.5 to 4 wt. % of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The component of the composition can include a scale inhibitor. The composition can comprise from about 0.1 to 20 wt. %, from about 0.5 to 10 wt. %, or from about 1 to 10 wt. % of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), and salts of a polymaleic acid/acrylic acid/acrylamidomethyl propane sulfonate terpolymer (PMA/AA/AMPS).

The component of the composition can include an emulsifier. The composition can comprise from about 0.1 to 10 wt. %, from about 0.5 to 5 wt. %, or from about 0.5 to 4 wt. % of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

The component of the composition can include a water clarifier. The composition can comprise from about 0.1 to 10 wt. %, from about 0.5 to 5 wt. %, or from about 0.5 to 4 wt. % of a water clarifier, based on total weight of the composition. Suitable water clarifiers include, but are not limited to, inorganic metal salts such as alum, aluminum chloride, and aluminum chlorohydrate, or organic polymers such as acrylic acid based polymers, acrylamide based polymers, polymerized amines, alkanolamines, thiocarbamates, and cationic polymers such as diallyldimethylammonium chloride (DADMAC).

The component of the composition can include a dispersant. The composition can comprise from about 0.1 to 10 wt. %, from about 0.5 to 5 wt. %, or from about 0.5 to 4 wt. % of a dispersant, based on total weight of the composition. Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The component of the composition can include an emulsion breaker. The composition can comprise from about 0.1 to 10 wt. %, from about 0.5 to 5 wt. %, or from about 0.5 to 4 wt. % of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

The component of the composition can include a hydrogen sulfide scavenger. The composition can comprise from about 1 to 50 wt. %, from about 1 to 40 wt. %, or from about 1 to 30 wt. % of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The component of the composition can include a gas hydrate inhibitor. The composition can comprise from about 0.1 to 25 wt. %, from about 0.5 to 20 wt. %, or from about 1 to 10 wt. % of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The component of the composition can include a kinetic hydrate inhibitor. The composition can comprise from about 0.1 to 25 wt. %, from about 0.5 to 20 wt. %, or from about 1 to 10 wt. % of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The component of the composition can include a biocide. The composition can comprise from about 0.1 to 10 wt. %, from about 0.5 to 5 wt. %, or from about 0.5 to 4 wt. % of a biocide, based on total weight of the composition. Suitable biocides include, but are not limited to, oxidizing and non-oxidizing biocides. Suitable non-oxidizing biocides include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)). Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, and peroxides.

The component of the composition can include a pH modifier. The composition can comprise from about 0.1 to 20 wt. %, from about 0.5 to 10 wt. %, or from about 0.5 to 5 wt. % of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The component of the composition can include a surfactant. The composition can comprise from about 0.1 to 10 wt. %, from about 0.5 to 5 wt. %, or from about 0.5 to 4 wt. % of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

Corrosion inhibitor compositions disclosed herein can further include additional functional agents or additives that provide a beneficial property. For example, additional agents or additives can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (i.e., dyes, odorants, perfumes), or other additives suitable for formulation with a corrosion inhibitor composition, and mixtures thereof. Additional agents or additives will vary according to the particular corrosion inhibitor composition being manufactured and its intend use as one skilled in the art will appreciate.

Alternatively, the compositions can not contain any of the additional agents or additives.

Additionally, the corrosion inhibitors of the invention can be formulated into compositions comprising the following components. These formulations include the ranges of the components listed and can optionally include additional agents.

| Component | 1 | 2 | 3 | 4 | 5 | 6 | 7 | 8 | 9 | 10 | 11 | 12 |
|---|---|---|---|---|---|---|---|---|---|---|---|---|
| Compound of Formula 1 or 2 | 0.1-20 | 0.1-20 | 0.1-20 | 0.1-20 | 0.1-20 | 0.1-20 | 10-20 | 10-20 | 10-20 | 10-20 | 10-20 | 0.1-20 |
| Organic solvent | 5-40 | — | 5-50 | — | 5-50 | 5-50 | 5-40 | — | 5-50 | — | — | 10-20 |
| Additional corrosion inhibitor | 0.1-20 | 0.1-20 | — | — | — | — | 0.1-20 | 0.1-20 | — | — | — | 0.1-20 |
| Asphaltene inhibitor | 0.1-5 | 0.1-5 | 0.1-5 | 0.1-5 | — | — | 0.1-5 | 0.1-5 | 0.1-5 | — | — | 0.1-5 |
| Scale inhibitor | 1-10 | 1-10 | 1-10 | 1-10 | 1-10 | — | 1-10 | 1-10 | 1-10 | 1-10 | — | 1-10 |
| Gas hydrate inhibitor | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| Water | 0.00 | 0-40 | 0-10 | 0-60 | 0-15 | 0-25 | 0.00 | 0-40 | 0-10 | 0-65 | 0-75 | |

| Component | 13 | 14 | 15 | 16 | 17 | 18 | 19 | 20 | 21 | 22 | 23 | 24 |
|---|---|---|---|---|---|---|---|---|---|---|---|---|
| Compound of Formula 1 or 2 | 0.1-20 | 0.1-20 | 0.1-20 | 0.1-20 | 0.1-20 | 0.1-20 | 10-20 | 10-20 | 10-20 | 10-20 | 10-20 | 10-20 |
| Organic solvent | — | 10-20 | — | 10-35 | 10-35 | — | 10-15 | — | — | 10-35 | 10-35 | — |
| Additional corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene inhibitor | 0.1-5 | — | — | — | — | — | 0.1-5 | — | — | — | — | — |
| Scale inhibitor | 1-10 | 1-10 | — | — | 1-10 | — | 1-10 | 1-10 | — | — | — | 1-10 |
| Gas hydrate inhibitor | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | 0.00 | 0-20 | 0-30 | 0-20 | 0.00 | 0-50 |

Another aspect of the invention is a method of inhibiting corrosion at a surface. The method comprises either: contacting the surface with an effective amount of a compound of formula (1) to inhibit corrosion on the surface; contacting the surface with a composition comprising an effective amount of the compound of formula (1) and a component comprising an organic solvent, a corrosion inhibitor, an asphaltene inhibitor, a paraffin inhibitor, a scale inhibitor, an emulsifier, a water clarifier, a dispersant, an emulsion breaker, a gas hydrate inhibitor, a biocide, a pH modifier, a surfactant, or a combination thereof to inhibit corrosion on the surface; or adding the compound or the composition to a fluid which contacts the surface to inhibit corrosion on the surface. The composition can be any composition as described herein.

The compounds/compositions can be used for inhibiting corrosion in oil and gas applications such as by treating a gas or liquid stream with an effective amount of a compound or composition as described herein. The compounds and compositions can be used in any industry where it is desirable to inhibit corrosion at a surface.

The compounds/compositions can be used in water systems, condensate/oil systems/gas systems, or any combination thereof. For example, the compounds/compositions can be used in controlling scale on heat exchanger surfaces.

The compounds/compositions can be applied to a gas or liquid produced, or used in the production, transportation, storage, and/or separation of crude oil or natural gas.

The compounds/compositions can be applied to a gas stream used or produced in a coal-fired process, such as a coal-fired power plant.

The compounds/compositions can be applied to a gas or liquid produced or used in a waste-water process, a farm, a slaughter house, a land-fill, a municipality waste-water plant, a coking coal process, or a biofuel process.

A fluid to which the compounds/compositions can be introduced can be an aqueous medium. The aqueous medium can comprise water, gas, and optionally liquid hydrocarbon.

A fluid to which the compounds/compositions can be introduced can be a liquid hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene.

The fluid or gas can be a refined hydrocarbon product.

A fluid or gas treated with a compound/composition can be at any selected temperature, such as ambient temperature or an elevated temperature. The fluid (e.g., liquid hydrocarbon) or gas can be at a temperature of from about 40° C. to about 250° C. The fluid or gas can be at a temperature of from −50° C. to 300° C., 0° C. to 200° C., 10° C. to 100° C., or 20° C. to 90° C. The fluid or gas can be at a temperature of 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. The fluid or gas can be at a temperature of 85° C., 86° C., 87° C., 88° C., 89° C., 90° C., 91° C., 92° C., 93° C., 94° C., 95° C., 96° C., 97° C., 98° C., 99° C., or 100° C.

The compounds/compositions can be added to a fluid at various levels of water cut. For example, the water cut can be from 0% to 100% volume/volume (v/v), from 1% to 80% v/v, or from 1% to 60% v/v. The fluid can be an aqueous medium that contains various levels of salinity. The fluid can have a salinity of 0% to 25%, about 1% to 24%, or about 10% to 25% weight/weight (w/w) total dissolved solids (TDS).

The fluid or gas in which the compounds/compositions are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be part of a coal-fired power plant. The apparatus can be a scrubber (e.g., a wet flue gas desulfurizer, a spray dry absorber, a dry sorbent injector, a spray tower, a contact or bubble tower, or the like). The apparatus can be a cargo vessel, a storage vessel, a holding tank, or a pipeline connecting the tanks, vessels, or processing units.

The compounds/compositions can be introduced into a fluid or gas by any appropriate method for ensuring dispersal through the fluid or gas.

The compounds/compositions can be added to the hydrocarbon fluid before the hydrocarbon fluid contacts the surface.

The compounds/compositions can be added at a point in a flow line upstream from the point at which corrosion prevention is desired.

The compounds/compositions can be injected using mechanical equipment such as chemical injection pumps, piping tees, injection fittings, atomizers, quills, and the like.

The compounds/compositions of the invention can be introduced with or without one or more additional polar or non-polar solvents depending upon the application and requirements.

The compounds/compositions can be pumped into an oil and/or gas pipeline using an umbilical line. A capillary injection system can be used to deliver the compounds/compositions to a selected fluid.

The compounds/compositions can be introduced into a liquid and mixed.

The compounds/compositions can be injected into a gas stream as an aqueous or non-aqueous solution, mixture, or slurry.

The fluid or gas can be passed through an absorption tower comprising compounds/compositions.

The compounds/compositions can be applied continuously, in batch, or a combination thereof. The compounds/compositions doses can be continuous to prevent corrosion. The compounds/compositions doses can be intermittent (i.e., batch treatment) or the compounds/compositions doses can be continuous/maintained and/or intermittent to inhibit corrosion.

The flow rate of a flow line in which the compound/composition is used can be between 0 and 100 feet per second, or between 0.1 and 50 feet per second. The compounds/compositions can also be formulated with water in order to facilitate addition to the flow line.

The compounds/compositions of the invention can be used for inhibiting corrosion in other applications.

The compounds/compositions are useful for corrosion inhibition of containers, processing facilities, or equipment in the food service or food processing industries. The compounds/compositions have particular value for use on food packaging materials and equipment, and especially for cold or hot aseptic packaging. Examples of process facilities in which the compounds/compositions can be employed include a milk line dairy, a continuous brewing system, food processing lines such as pumpable food systems and beverage lines, ware wash machines, low temperature ware wash machines, dishware, bottle washers, bottle chillers, warmers, third sink washers, processing equipment such as tanks, vats, lines, pumps and hoses (e.g., dairy processing equipment for processing milk, cheese, ice cream and other dairy products), and transportation vehicles. The compounds/compositions can be used to inhibit corrosion in tanks, lines, pumps, and other equipment used for the manufacture and storage of soft drink materials, and also used in the bottling or containers for the beverages.

The compounds/compositions can also be used on or in other industrial equipment and in other industrial process streams such as heaters, cooling towers, boilers, retort waters, rinse waters, aseptic packaging wash waters, and the like. The compounds/compositions can be used to treat surfaces in recreational waters such as in pools, spas, recreational flumes and water slides, fountains, and the like.

The compounds/compositions can be used to inhibit the corrosion of metal surfaces contacted with cleaners in surfaces found in janitorial and/or housekeeping applications, food processing equipment and/or plant applications, and in laundry applications. For example, the corrosion of washers, such as tunnel washers for washing textiles, can be inhibited according to methods disclosed herein.

The compounds/compositions can be used or applied in combination with low temperature dish and/or warewash sanitizing final rinse, toilet bowl cleaners, and laundry bleaches. The compounds, compositions and methods can be used to treat metal surfaces, such as ware, cleaned and/or sanitized with corrosive sources.

The compounds, compositions and methods disclosed herein protect surfaces from corrosion caused by hypochlorite bleach. A method can include providing the corrosion inhibitor compounds/compositions to a surface treated with a hypochlorite solution in order to inhibit corrosion caused by the hypochlorite solution. The method can include preparing an aqueous use composition of the present corrosion inhibitor composition. The method can further include contacting a surface, such as a hard metal surface, in need of corrosion inhibition due to contact with a hypochlorite solution.

The compounds/compositions can be dispensed by immersing either intermittently or continuously in water. The composition can then dissolve, for example, at a controlled or predetermined rate. The rate can be effective to maintain a concentration of dissolved agent that is effective for use according to the methods disclosed herein.

The term "alkyl," as used herein, refers to a linear or branched hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons). Alkyl groups include, but are not limited to, methyl, ethyl, n-propyl, isopropyl, n-butyl, iso-butyl, secondary-butyl, and tertiary-butyl. Alkyl groups may be unsubstituted or substituted by one or more suitable substituents, as defined above.

The term "alkenyl," as used herein, refers to a straight or branched hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like, optionally substituted by one or more suitable substituents, preferably 1 to 5 suitable substituents, as defined above.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle" or "heterocyclyl," as used herein, refers to a monocyclic, bicyclic, or tricyclic group containing 1 to 4 heteroatoms selected from N, O, $S(O)_n$, $P(O)_n$, $PR_z$, NH or $NR_z$, wherein $R_z$ is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "hydroxy," as used herein, refers to an —OH group.

The term "suitable substituent," as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The term "water cut," as used herein, means the percentage of water in a composition containing an oil and water mixture.

Having described the invention in detail, it will be apparent that modifications and variations are possible without departing from the scope of the invention defined in the appended claims.

EXAMPLES

The following non-limiting examples are provided to further illustrate the invention.

Example 1: Synthesis of Compounds

The compounds were prepared by reacting ethoxylated triethylenetetramine (TETA) (commercially available from Huntsman as surfactant 2147) with specified amounts of fatty acid(s).

Surfactant 2147 available from Huntsman (Ethoxylated TETA, 75% aqueous solution) was added to a three-necked round bottom flask equipped with a Dean Stark apparatus, nitrogen inlet, magnetic stir bar, and a condenser. The flask was heated to a temperature of 120° C. and water present in surfactant 2147 was removed using the Dean Stark apparatus. A fatty acid was then introduced into the flask. The mixture was heated for at least 6 hours at 160-180° C. to remove water of reaction using the Dean Stark apparatus. The product obtained from this step essentially consisted of a mixture of mono-, di-, tri-, tetra-, penta-, and hexa-esterified products. The average molar ratio of surfactant 2147 to fatty acid was in range of 1 to 4.

Different compounds were created by varying amounts of the fatty acid with respect to the polyhydroxypolyamine compound.

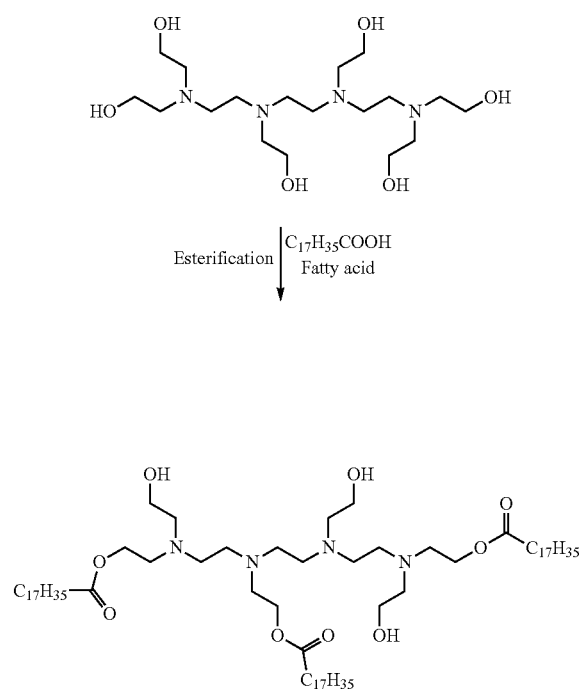

Scheme 1

TABLE 1

Description of samples synthesized

| Sample | Polyol | Acid |
|--------|--------|------|
| NQ-71 | Surfactant 2147 | Stearic acid |
| NQ-75 | Surfactant 2147 | TOFA (R-605) |
| NQ-73 | Surfactant 2147 | Palmitic acid |
| NQ-77 | Surfactant 2147 | Oleic acid |
| NQ-83 | Surfactant 2147 | Behenic Acid |
| NQ-81 | Surfactant 2147 | Myristic Acid |
| NQ-79 | Surfactant 2147 | Stearic + Palmitic acid |

The quaternary ammonium salts of the present invention were prepared by a two-step reaction as depicted by a representative example (using $C_{18}$ fatty acid) in scheme 2.

The process described above was used to obtain the polyester polyamines.

The polyester polyamines prepared above (NQ-XX) were then reacted with methyl chloride to obtain quaternized products (Q-XX series).

Scheme 2

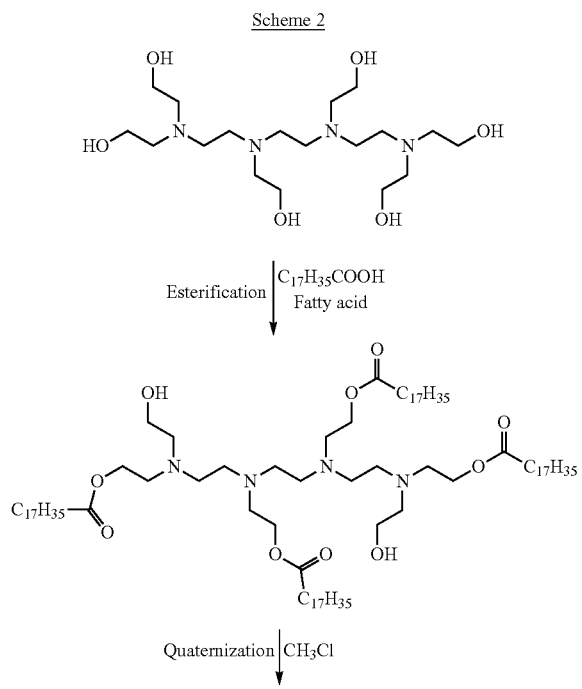

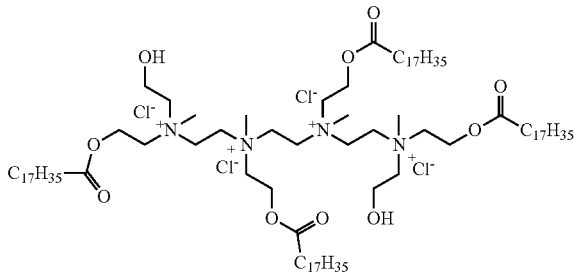

Quaternization of Esterification Product (Q-XX): Esteramine (NQ-XX) and isopropanol were charged to a Parr reactor and agitation was turned on. A vacuum of 28 inches of mercury was applied for 5 minutes and the reactor was heated to 60-65° C. When the temperature reached 65° C., methyl chloride ($CH_3Cl$) was charged to 10 psig. The temperature was increased to 80° C. and the $CH_3Cl$ pressure was maintained at less than 40 psig. When the $CH_3Cl$ addition was complete, temperature was maintained at 90-93° C. for an hour. The total amine value (TAV) and acid value (AV) of the reaction mixture was checked (<2%). Sodium hydroxide (NaOH, 50% aqueous) was added to adjust the acid value (to <2%) or extra $CH_3Cl$ was charged to adjust the TAV (to <2%), and the reaction mixture was reacted at 90° C. for an additional hour. On completion, the reaction mixture was cooled to 50° C. and the pH was adjusted to 5.5-8.5 with 50% caustic solution. The reaction mixture was mixed well and a slight vacuum (about 12 inches of mercury) was applied to the reaction mixture for 5 minutes. The non-volatile residue (NVR, Mettler method) measurement was adjusted to 50% with IPA.

TABLE 2

Quaternized polyesters synthesized

| Raw Material | Weight EXP #1 Q-24 | Weight EXP #2 Q-38 | Weight EXP #3 Q-39 | Weight EXP #4 Q-42 | Weight EXP #5 Q-43 | Weight EXP #6 Q-44 | Weight EXP #7 Q-45 |
|---|---|---|---|---|---|---|---|
| NQ-75 (TOFA ester) | 95 | | | | | | |
| $CH_3Cl$ | 14 | 14 | 15.4 | 14.25 | 17.1 | 16.8 | 12.5 |
| NaOH (50%) | 0.9 | 1 | 3 | 1 | 1 | 1.5 | 1 |
| IPA | 95 | 90 | 95 | 95 | 110 | 95 | 95 |
| NQ-77 (Oleic acid ester) | | 92.5 | | | | | |
| NQ-73 (Palmitic acid ester) | | | 95 | | | | |
| NQ-71 (Stearic acid ester) | | | | 95 | | | |
| NQ-79 (Stearic + Palmitic acid ester) | | | | | 110 | | |
| NQ-81 (Myristic acid ester) | | | | | | 95 | |
| NQ-83 (Behenic acid ester) | | | | | | | 95 |
| Total Raw Material | 204.9 | 197.5 | 208.4 | 205.25 | 238.1 | 208.3 | 203.5 |

Example 2: Corrosion Testing

The corrosion inhibition for these compounds were measured using corrosion bubble cell tests performed using the following conditions for polyamine-polyester chemistry. The temperature was 80° C. and carbon dioxide saturated fluids having 80 vol % of a brine (e.g., 3 wt % sodium chloride brine) and 20 vol % LVT-200 hydrocarbon (i.e., hydrotreated light petroleum distillates) having a continuous carbon dioxide sparge at atmospheric pressure. There was about 3 hours pre-corrosion time (i.e. with no corrosion inhibitor) before 20 ppm (based on the weight of the water phase) of a 10 wt % active of polyamine-polyester chemistry with 1 wt % 2-mercaptoethanol in solvent blend was added. This equates to 2 ppm of the active chemistry with 0.2 ppm 2-mercaptoethanol being introduced into the test cell.

A comparison with a commonly used quaternary chemistry and imidazoline chemistry was made at the same actives along with the same activity of 2-mercaptoethanol and dose rate. A low concentration was purposefully used in order to differentiate between the chemistries.

The corrosion inhibition results for the non-quaternized compounds are given in the table below as well as shown in FIG. 1. The data show that, under these conditions and dose rates, based on the % protection, all the polyamine-polyester compounds significantly exceed the performance of the commonly used incumbent chemistries.

| Candidate Chemistry | 2-Mercaptoethanol Activity (%) | Candidate Chemistry Activity (%) | Dosage (ppm) | Corrosion Rate After 15 h of Cl Injection (mpy) | % Protection |
|---|---|---|---|---|---|
|  |  |  | 0 | 500 | N/A |
| dimethyl benzyl ammonium chloride (DMBAC) | 1 | 10 | 20 | 339 | 32 |
| TOFA:DETA imidazoline salted with acetic acid | 1 | 10 | 20 | 432 | 14 |
| NQ-71 (Stearic acid ester) | 1 | 10 | 20 | 58 | 88 |
| NQ-75 (TOFA ester) | 1 | 10 | 20 | 64 | 87 |
| NQ-73 (Palmitic acid ester | 1 | 10 | 20 | 70 | 86 |
| NQ-77 (Oleic acid ester) | 1 | 10 | 20 | 82 | 84 |
| NQ-83 (Behenic acid ester) | 1 | 10 | 20 | 43 | 91 |
| NQ-81 (Myristic acid ester) | 1 | 10 | 20 | 79 | 84 |
| NQ-79 (Stearic and palmitic acid ester) | 1 | 10 | 20 | 88 | 82 |

Figure 2:
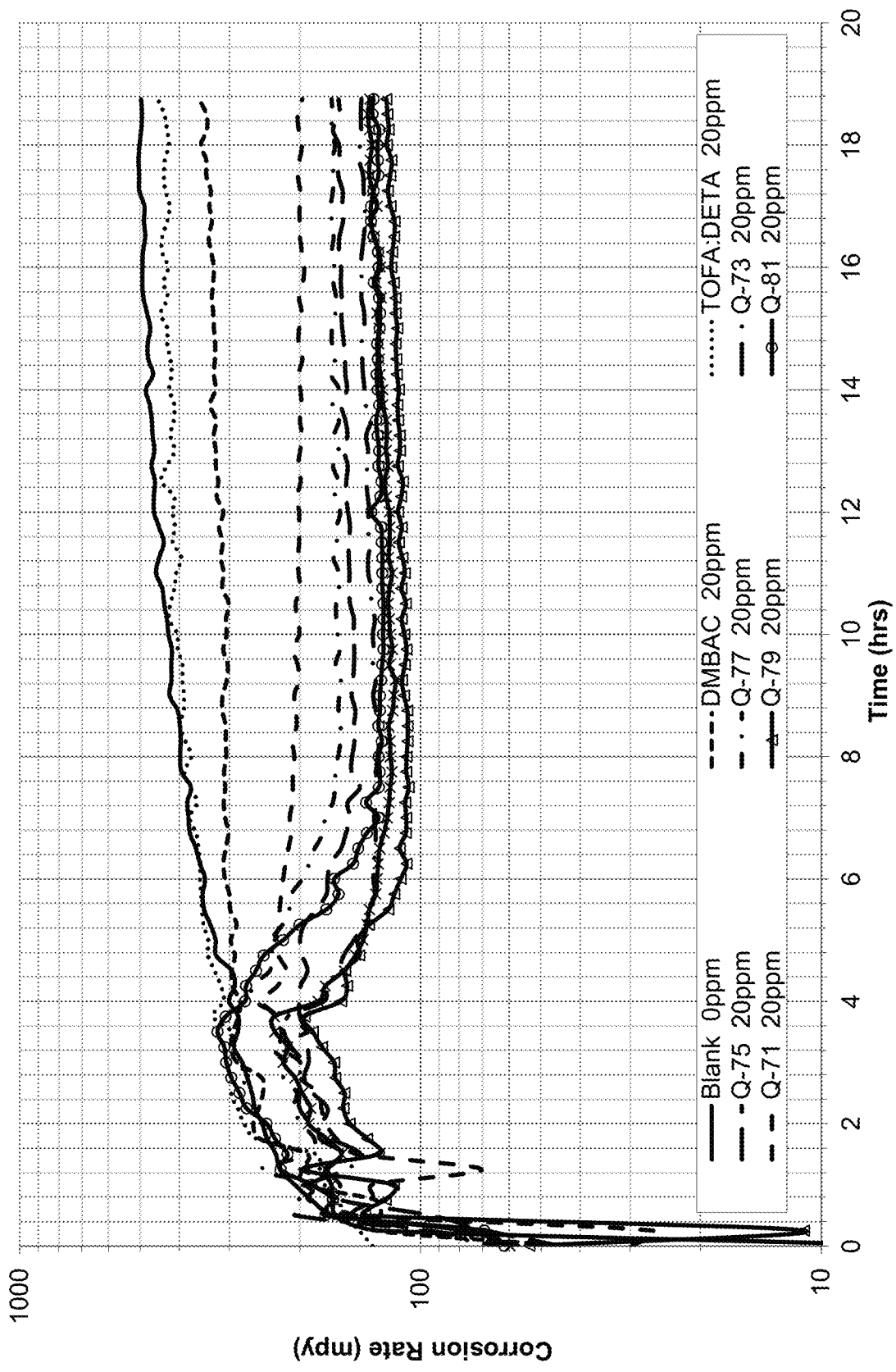
FIG. 2 is a graph of the corrosion rate (mpy) versus time (hours) for various corrosion inhibitor compositions.

The corrosion inhibition results for the quaternized compounds using the method described above are given in the table below as well as shown in FIG. 2.

The data show that, under these conditions and dose rates, based on the % protection, all the polyamine polyester compounds significantly exceed the performance of the commonly used incumbent compounds.

| Candidate Chemistry | 2-Mercaptoethanol Activity (%) | Candidate Chemistry Activity (%) | Dosage (ppm) | Corrosion Rate After 13 h of Cl Injection (mpy) | % Protection |
|---|---|---|---|---|---|
|  | N/A | N/A | 0 | 486 | N/A |
| Dimethyl benzyl ammonium chloride (DMBAC) | 1 | 10 | 20 | 338 | 30 |
| TOFA:DETA imidazoline salted with acetic acid | 1 | 10 | 20 | 441 | 9 |
| Q-75 TOFA Quat | 1 | 10 | 20 | 159 | 67 |
| Q-77 Oleic Acid Quat | 1 | 10 | 20 | 165 | 66 |
| Q-73 Palmitic Acid Quat | 1 | 10 | 20 | 139 | 71 |
| Q-71 Stearic Acid Quat | 1 | 10 | 20 | 200 | 59 |
| Q-79 Stearic Acid + Palmitic Acid Quat | 1 | 10 | 20 | 116 | 76 |
| Q-81 Myristic Acid Quat | 1 | 10 | 20 | 131 | 73 |
| Q-83 Behenic Acid Quat | 1 | 10 | 20 | 130 | 73 |

Example 3: Softness Testing

Figure 3:
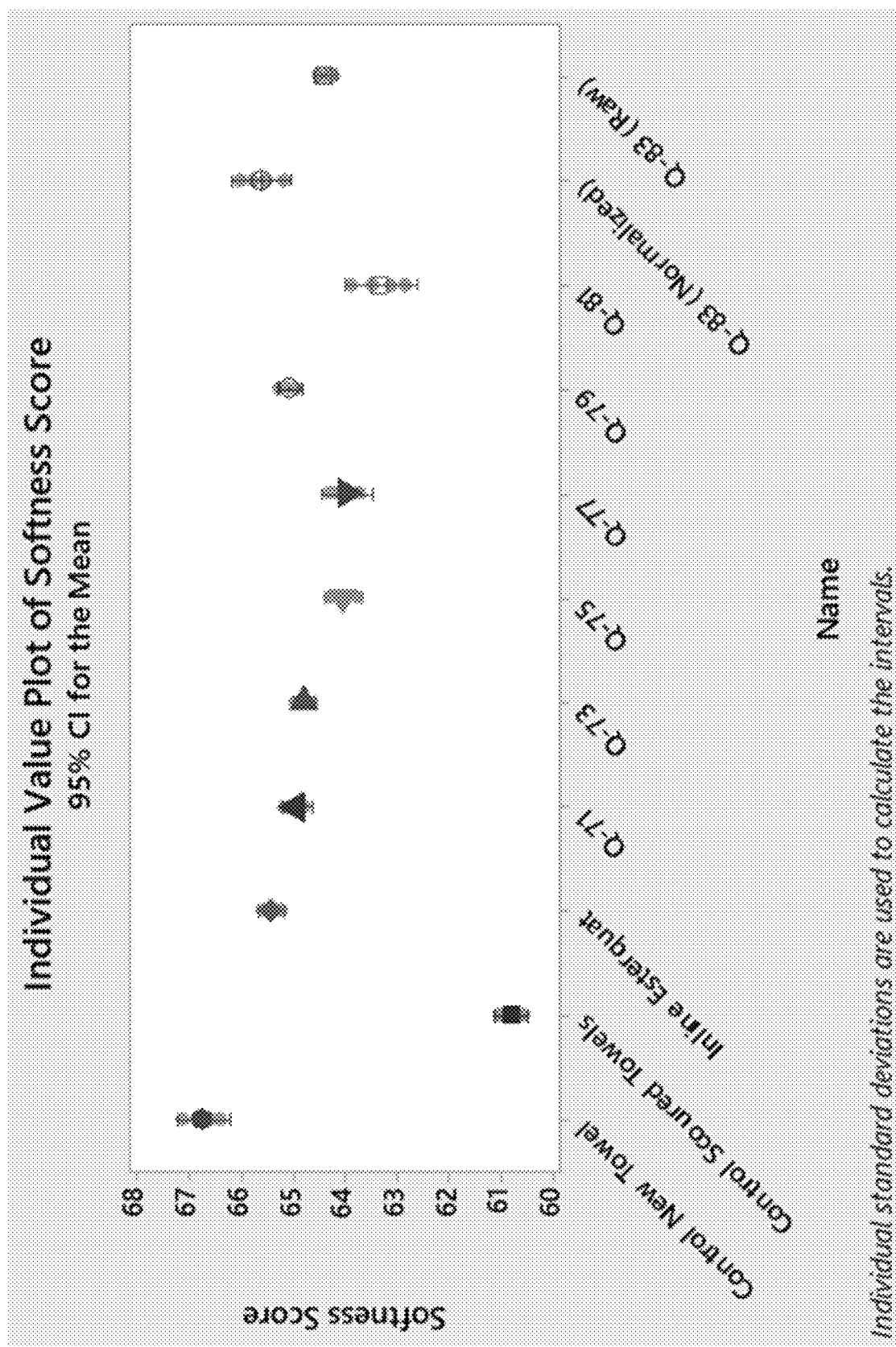
FIG. 3. is a graph of the softness score for various compositions.

The softness of the compounds was also measured as described below. The treated samples were compared against scoured (no treatment) samples. As can be seen in FIG. 3, at least three compounds (actives) of Formula 1 and 2 match the performance of the control compound of a commercial quaternary corrosion inhibitor dosed at equivalent levels.

The compounds were used to treat fabrics and the resulting softness of the fabrics was tested. Hand towels can be severely damaged by washing them using large amounts of caustic, hard water, and long dry times with high heat. After damaging these towels the phabrometer can determine the efficiency of various softening agents. This is determined by observing whether or not the fabric's softness qualities can be restored to their original state.

Samples were prepared for Phabrometer analysis as follows: (1) gather enough hand towels so that there will be at least 4 sample swatches per condition to be tested (one hand towel should provide at least eight swatches); (2) use tach-its to label each sample hand towel; (3) run five double scouring cycles (Unimac+Huebsch cycle 53) with a load weight of approximately 28 lbs. and drying between each cycle; (4)(a) when scouring, connect the washer to 17 gpg water; (4)(b) add 70 g L2000 XP to supply cup 1 and 2; (5)(a) use the die press and 11.3 cm circular die cut to cut sample swatches from all of the scoured hand towels, (5)(b) when cutting sample swatches, lay each hand towel in the die press with the same orientation e.g. the tag of the towel is always facing up, (5)(c) stack all the sample swatches maintaining the previously established orientation; (6) to label the sample swatches, fold them in half and tach-it through the center of the swatch, while still maintaining the same orientation for all swatches (recall that there should be 4 sample swatches per condition); (7) place all 1500 mL beakers on the hotplate and add one stir bar and 750 mL) of DI water to each beaker. Alternatively, steps 6-10 can be done in launderometer cups instead of in beakers on a benchtop, (7)(a) connect the temperature probe to the hot plate and place it in one of the beakers, (7)(b) set the temperature of the hot plate to 40° C. and the stir bars to spin at 400 RPM; (8) deliver 100 ppm of Aquanomic 2.0 Detergent and 500 ppm of Aquanomic 2.0 Builder to each beaker or launderometer container. Let it sit for 6 minutes at the temperature specified above. When finished, rinse well in DI water and extract (see 10); (9) repeat step 6 for the softening step; (10) deliver a specific amount of softening agent to each beaker to achieve the desired concentration adjusted to 750 mL/1000 mL total volume, then allow each solution to mix thoroughly and reach the desired temperature; (11) when the solutions are thoroughly mixed and at temperature, start a stopwatch and add swatches one at a time to their respective beakers and let mix for 6 minutes (if the swatches are limiting the stir bars ability to agitate the mixture, use a spatula to adjust the swatches); (12) after 6 minutes, empty the solution from each beaker and extract all of the treated sample swatches for 90 seconds, (12)(a) when extracting the sample swatches, ensure that the apparatus is balanced properly for smooth extraction, (12)(b) extract only four samples at a time to guarantee that different conditions are not interfering with one another; (13) dry all four swatches of the same condition for 20 minutes in a homestyle dryer, or dry all swatches at once in a drying cabinet for 30 minutes with high heat; (14) repeat steps 6-11 for three times (3 cycles test) or for the number of cycles specified; (15) place all treated swatches in a humidity chamber and allow them to sit overnight at 40% humidity; (16) remove swatches from humidifier and sort into small stacks by treatment condition.

The fabric analysis was performed as follows: (1) power on the Phabrometer 3 FES found in Lab F54 and open the PhES software; (2) connect the Phabrometer to the computer by selecting the light bulb icon on the toolbar. Confirm that the computer is connected to the Phabrometer by looking for 4 green circles and 2 yellow squares within the "Communication Status" window; (3) in order to collect and record data, the PhES software must be connected to a database. This is done by selecting the blue scroll on the toolbar and opening the "NCTFabricData" Microsoft Access file; (4) to begin collecting data, select the blue paper icon located within the "Fabric Profile" window and a new dialogue box will open that will be used to classify each sample. The fabric profile requires the following inputs: (a) for terry cotton towels, the dencity type selected should be "Heavy Fabric (H)", (b) the fabric must have a unique name within the class/group selected, (c) remove the tach-it(s) from the swatch and use a lab balance to determine the weight of individual swatches in grams and record this value, (d) use a digital thickness gauge to measure the thickness of individual swatches in three spots and record the average of those values, (e) swatches can be sorted using classes and groupings. Having a designated class is required, but groups are optional for further breakdown of conditions, (f) number of specimen should be set to 1 for independent swatch results, or increased to the number of replicates if automatic averaging is desired; (5) select "Save" once the fabric profile is complete and place the swatch in the test base of the Phabrometer. *NOTE: Swatches should always be placed in the Phabrometer with the same orientation. This orientation can vary from the one used when preparing samples, but must be consistent throughout the entire duration of analysis; (6) close the door of the Phabrometer and select the "Run Sample" icon; (7) once the Phabrometer returns to its starting state, select the "Save" icon (FIG. 5) and remove the swatch from the test base; (8) repeat steps 4-7 for all swatches; (9) select "Tools" on the toolbar, then select "Export Attributes to Excel . . . "; (10) open the Phabrometer door and use compressed air to remove any strands or pieces of linen from inside the Phabrometer; (11) select the "Exit" icon on the toolbar to close the PhES software and then power down the Phabrometer 3 FES.

The fabric used was cotton terry and the process described above was used with 1 L launderometer cups at 0.12 g/L active in deionized water.

| Sample Name | Resilience Score | Softness Score | Smoothness Score | Chemistry |
|---|---|---|---|---|
| NQ-71 | 56.1409 | 60.8755 | 51.1848 | C18 Stearic Acid |
| NQ-71 | 54.6804 | 62.1325 | 50.996 | C18 Stearic Acid |
| NQ-75 | 60.5183 | 60.6798 | 51.9184 | TOFA |
| NQ-75 | 57.643 | 60.7765 | 51.3344 | TOFA |
| NQ-73 | 59.0682 | 60.7371 | 51.3689 | C16 Palmitic Acid |
| NQ-73 | 54.6949 | 61.6188 | 51.5257 | C16 Palmitic Acid |

-continued

| Sample Name | Resilience Score | Softness Score | Smoothness Score | Chemistry |
|---|---|---|---|---|
| NQ-77 | 56.3351 | 62.3267 | 51.8823 | Oleic Acid |
| NQ-77 | 58.4707 | 60.8965 | 51.6836 | Oleic Acid |
| NQ-83 | 59.0285 | 60.9999 | 51.7369 | C22 Behenic Acid |
| NQ-83 | 56.6863 | 61.4102 | 51.4461 | C22 Behenic Acid |
| NQ-81 | 58.2222 | 60.426 | 51.4281 | C14 Myristic Acid |
| NQ-81 | 58.206 | 60.5285 | 51.6543 | C14 Myristic Acid |
| NQ-79 | 59.5951 | 61.2062 | 51.9909 | C17 Stearic + Palmitic Acid |
| NQ-79 | 57.3509 | 61.3463 | 51.6459 | C17 Stearic + Palmitic Acid |
| Q-83 (Quat 7) | 48.5212 | 64.3544 | 51.1948 | C22 Behenic Acid |
| Q-83 (Quat 7) | 48.4251 | 64.4817 | 51.3664 | C22 Behenic Acid |
| Q-83 (Quat 7) | 48.876 | 64.1903 | 51.3963 | C22 Behenic Acid |
| Q-83 (Quat 7) | 49.5791 | 64.4833 | 51.4969 | C22 Behenic Acid |
| Control (new towel) | 45.144 | 66.5582 | 51.9272 | Control New Towel |
| Control (new towel) | 44.7265 | 66.3625 | 51.8111 | Control New Towel |
| Control (new towel) | 44.6035 | 66.8125 | 51.9729 | Control New Towel |
| Control (new towel) | 44.1442 | 67.1022 | 51.9742 | Control New Towel |
| Q-75 (Quat 1) | 50.9956 | 64.0664 | 51.8104 | TOFA |
| Q-75 (Quat 1) | 50.8427 | 64.0276 | 51.8837 | TOFA |
| Q-75 (Quat 1) | 52.0989 | 63.7354 | 51.8257 | TOFA |
| Q-75 (Quat 1) | 50.8017 | 64.2817 | 51.8691 | TOFA |
| Q-77 (Quat 2) | 50.3284 | 64.2786 | 51.8339 | Oleic Acid |
| Q-77 (Quat 2) | 50.0969 | 64.1536 | 51.7368 | Oleic Acid |
| Q-77 (Quat 2) | 51.3563 | 63.6994 | 51.694 | Oleic Acid |
| Q-77 (Quat 2) | 52.0713 | 63.6976 | 51.7739 | Oleic Acid |
| Q-73 (Quat 3) | 48.9912 | 64.6195 | 51.7653 | C16 Palmitic Acid |
| Q-73 (Quat 3) | 48.9598 | 64.8171 | 51.8529 | C16 Palmitic Acid |
| Q-73 (Quat 3) | 48.6458 | 64.7024 | 51.771 | C16 Palmitic Acid |
| Q-73 (Quat 3) | 48.5031 | 64.9244 | 51.7322 | C16 Palmitic Acid |
| Q-71 (Quat 4) | 47.81 | 65.1442 | 51.8286 | C18 Stearic Acid |
| Q-71 (Quat 4) | 47.892 | 64.7567 | 51.4696 | C18 Stearic Acid |
| Q-71 (Quat 4) | 48.6373 | 64.9738 | 51.7701 | C18 Stearic Acid |
| Q-71 (Quat 4) | 47.6769 | 64.7963 | 51.4552 | C18 Stearic Acid |
| Q-79 (Quat 5) | 48.5573 | 65.2516 | 51.9265 | C17 Stearic + Palmitic Acid |
| Q-79 (Quat 5) | 48.085 | 65.0693 | 51.7013 | C17 Stearic + Palmitic Acid |
| Q-79 (Quat 5) | 48.8756 | 64.9208 | 51.8922 | C17 Stearic + Palmitic Acid |
| Q-79 (Quat 5) | 48.9053 | 64.9385 | 51.6928 | C17 Stearic + Palmitic Acid |
| Q-81 (Quat 6) | 53.7244 | 62.835 | 51.6168 | C14 Myristic Acid |
| Q-81 (Quat 6) | 50.9149 | 63.4498 | 51.3493 | C14 Myristic Acid |
| Q-81 (Quat 6) | 51.9574 | 63.0949 | 51.3833 | C14 Myristic Acid |
| Q-81 (Quat 6) | 51.0002 | 63.8573 | 51.7254 | C14 Myristic Acid |
| inline Esterquat | 47.8217 | 65.369 | 51.7735 | Control inline Esterquat |
| inline Esterquat | 47.5518 | 65.2225 | 51.6806 | Control inline Esterquat |
| inline Esterquat | 47.1478 | 65.4954 | 51.6828 | Control inline Esterquat |
| inline Esterquat | 46.8979 | 65.566 | 51.6974 | Control inline Esterquat |
| Scoured Towel Control (No treatment) | 59.7937 | 61.0322 | 51.6551 | Control Scoured Towels |
| Scoured Towel Control | 59.4237 | 60.8338 | 51.3812 | Control Scoured Towels |
| Scoured Towel Control | 59.185 | 60.729 | 51.5067 | Control Scoured Towels |
| Scoured Towel Control | 59.0405 | 60.5695 | 51.1855 | Control Scoured Towels |
| Q-83 (Quat 7) | 48.5212 | 64.3544 | 51.1948 | C22 Behenic Acid (Raw) |
| Q-83 (Quat 7) | 48.4251 | 64.4817 | 51.3664 | C22 Behenic Acid (Raw) |
| Q-83 (Quat 7) | 48.876 | 64.1903 | 51.3963 | C22 Behenic Acid (Raw) |
| Q-83 (Quat 7) | 49.5791 | 64.4833 | 51.4969 | C22 Behenic Acid (Raw) |
| Q-83 (Quat 7) | | 65.98459579 | | C22 Behenic Acid (Normalized) |
| Q-83 (Quat 7) | | 65.73030958 | | C22 Behenic Acid (Normalized) |
| Q-83 (Quat 7) | | 65.1522949 | | C22 Behenic Acid (Normalized) |
| Q-83 (Quat 7) | | 65.49829323 | | C22 Behenic Acid (Normalized) |

The terms "comprise(s)," "include(s)," "having," "has," "can," "contain(s)," and variants thereof, as used herein, are intended to be open-ended transitional phrases, terms, or words that do not preclude the possibility of additional steps or components. The singular forms "a," "and," "the" and "said" include plural references unless the context clearly dictates otherwise. The present disclosure also contemplates other embodiments "comprising," "consisting of" and "consisting essentially of," the embodiments or elements presented herein, whether explicitly set forth or not.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

What is claimed is:

1. A polyester polyamine compound, the polyester polyamine compound corresponding to the structure of Formula 2, or a salt thereof:

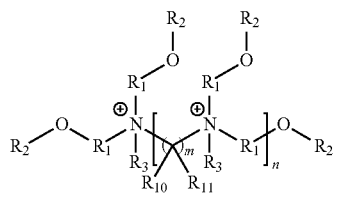

(2)

wherein
  $R_1$ is independently alkylene;
  $R_2$ is independently hydrogen or $-COR_4$;
  $R_3$ is independently alkyl, alkenyl, aryl, or alkaryl;
  $R_4$ is independently alkyl or alkenyl;
  $R_{10}$ and $R_{11}$ are each independently hydrogen, alkyl, or alkaryl;
  m is an integer from 1 to 10;
  n is an integer from 3 to 10; and
  wherein at least one $R_2$ is $-COR_4$.

2. The polyester polyamine compound of claim 1, wherein $R_1$ is $C_1$ to $C_8$ alkylene.

3. The polyester polyamine compound of claim 2, wherein $R_1$ is $-CH_2CH_2-$ or $-CH_2CH(CH_3)-$.

4. The polyester polyamine compound of claim 1, wherein from about 50% to about 100% of $R_2$ are $-COR_4$.

5. The polyester polyamine compound of claim 1, wherein $R_4$ is $C_{12}$ to $C_{22}$ alkyl.

6. The polyester polyamine compound claim 4, wherein $COR_4$ is derived from a fatty acid.

7. The polyester polyamine compound of claim 6, wherein the fatty acid is stearic acid, palmitic acid, oleic acid, behenic acid, myristic acid, or a combination thereof.

8. The polyester polyamine compound of claim 1, wherein $R_3$ is $C_1$ to $C_4$ alkyl or alkaryl.

9. The polyester polyamine compound of claim 1, wherein m is an integer from 2 to 6.

10. The polyester polyamine compound of claim 1, wherein $R_{10}$ is hydrogen and $R_{11}$ is hydrogen or methyl.

11. The polyester polyamine compound of claim 1, wherein n is an integer of 3, 4, or 5.

12. The polyester polyamine compound of claim 1, wherein the polyester polyamine compound is a halogen salt, a sulfate, or an acetate salt.

13. The polyester polyamine compound of claim 12, wherein the polyester polyamine compound is a chloride salt.

14. A corrosion inhibitor composition, wherein the composition comprises a component and a polyester polyamine compound corresponding to the structure of Formula 1 or 2, or a salt thereof:

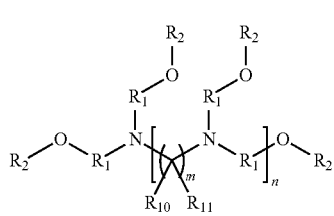

(1)

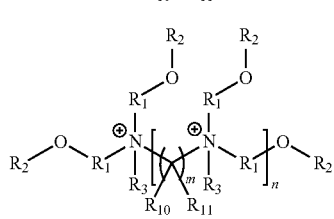

(2)

wherein
  $R_1$ is independently alkylene;
  $R_2$ is independently hydrogen or $-COR_4$;
  $R_3$ is independently alkyl, alkenyl, aryl, or alkaryl;
  $R_4$ is independently alkyl or alkenyl;
  $R_{10}$ and $R_{11}$ are each independently hydrogen, alkyl, or alkaryl;
  m is an integer from 1 to 10;
  n is an integer from 3 to 10; and
  wherein at least one $R_2$ is $-COR_4$.

15. The corrosion inhibitor composition of claim 14, wherein the component comprises one or more additional corrosion inhibitors, solvents, asphaltene inhibitors, paraffin inhibitors, scale inhibitors, emulsifiers, water clarifiers, dispersants, emulsion breakers, gas hydrate inhibitors, biocides, pH modifiers, or surfactants.

16. A method for inhibiting corrosion of a surface, the method comprising adding the corrosion inhibitor composition of claim 14 to a fluid which contacts the surface.

17. The method of claim 16, wherein the polyester polyamine compound is present in the fluid in an amount from about 1 ppm to about 5000 ppm.

18. A fabric softener composition, wherein the composition comprises the polyester polyamine compound of claim 1.

19. A method for treating fabric, the method comprising adding a composition comprising the polyester polyamine compounds of claim 1 to a fluid which contacts the fabric.

20. A fabric antistatic composition, a fabric conditioner composition, or a relaxant composition, wherein the composition comprises the polyester polyamine compound of claim 1.

* * * * *